United States Patent [19]

Gelfand

[11] 4,006,195
[45] Feb. 1, 1977

[54] PROCESS FOR THE CATALYTIC PRODUCTION OF DICHLOROTOLUENES

[75] Inventor: Samuel Gelfand, Niagara Falls, N.Y.

[73] Assignee: Hooker Chemicals & Plastics Corporation, Niagara Falls, N.Y.

[22] Filed: Sept. 10, 1975

[21] Appl. No.: 612,071

Related U.S. Application Data

[63] Continuation of Ser. No. 420,992, Dec. 3, 1973, abandoned, which is a continuation-in-part of Ser. No. 204,740, Dec. 3, 1971, abandoned.

[52] U.S. Cl. .......................................... 260/650 R
[51] Int. Cl.$^2$ ........................................ C07C 25/04
[58] Field of Search .............................. 260/650 R

[56] References Cited

UNITED STATES PATENTS

| | | | |
|---|---|---|---|
| 1,946,040 | 2/1934 | Stoesser et al. | 260/650 R |
| 2,473,990 | 6/1949 | Darragh | 260/650 R |
| 2,608,591 | 8/1952 | Lawlor | 260/650 R |
| 2,976,330 | 3/1961 | Guerin | 260/650 R |
| 3,226,447 | 12/1965 | Bing et al. | 260/650 R |
| 3,366,968 | 1/1968 | DiBella | 260/650 R |
| 3,711,562 | 1/1973 | Maul et al. | 260/649 R |
| 3,711,563 | 1/1973 | Carlson et al. | 260/649 R |
| 3,714,274 | 1/1973 | Rosenberg | 260/649 R |
| 3,752,856 | 8/1973 | Nagy et al. | 260/650 R |

FOREIGN PATENTS OR APPLICATIONS

778,642  7/1957  United Kingdom ........... 260/650 R

OTHER PUBLICATIONS

Kovacic et al., J. Am. Chem. Soc. 76, 5491–5494, (1954).

*Primary Examiner*—D. Horwitz
*Attorney, Agent, or Firm*—Peter F. Casella; William J. Crossetta, Jr.

[57] ABSTRACT

An improved process for the catalytic production of dichlorotoluenes, especially 2,4-dichlorotoluene, formed by reacting para-chlorotoluene with chlorine in the presence of a catalyst to form a mixture of chlorinated toluenes and thereafter separating from said mixture a dichlorotoluene fraction containing 2,4-dichlorotoluene, the improvement comprising reacting para-chlorotoluene in the liquid phase with chlorine gas in the presence of antimony trichloride catalyst. The mixed chlorotoluene product obtained contains in excess of 85% 2,4-dichlorotoluene, which mixture is then treated with a base, catalyst is removed by separation or filtration and the remaining product is distilled to yield a substantially pure 2,4-dichlorotoluene product.

4 Claims, No Drawings

PROCESS FOR THE CATALYTIC PRODUCTION OF DICHLOROTOLUENES

This is a continuation of application Ser. No. 420,992, filed Dec. 3, 1973 which is a continuation-in-part of application Ser. No. 204,740, filed Dec. 3, 1971, both now abandoned.

BACKGROUND OF THE INVENTION

There has been a rapidly increasing demand for di-chlorinated toluenes for use as both high boiling solvents and as intermediates in the preparation of pharmaceuticals, dye stuffs, rubber chemicals, and other organic compounds. Especially desirable is the 2,4-dichlorotoluene isomer, as compared to the less desirable 3,4-dichlorotoluene and 2,5-dichlorotoluene isomers. 2,4-dichlorotoluene has been shown to be especially suitable as an intermediate in the formation of herbicides, such as those under U.S. Pat. No. 3,617,252, having qualities which are more compatible with man's increased awareness of environmental and ecological stabilization. Of primary ecological importance is that lesser quantities can be used, to the same herbicidal effect of popular commercial herbicides, thereby causing less pollution. In view of these advantages, commercial output has been projected as increasing substantially in the coming years to production rates in excess of several million pounds per year. Accordingly, improvements to the process of preparing 2,4-dichlorotoluene in higher yields and with more conveniently available commercial raw materials has taken on a greater importance.

Heretofore, dichlorotoluenes have been produced by chloriuating toluene or parachlorotoluene in the presence of iron, zirconium tetrachloride or other known catalysts to form a chlorotoluene product that contains 2,4-dichlorotoluene along with substantial amounts of the less desirable 3,4-dichlorotoluene and 2,5-dichlorotoluene isomers, and quantities of trichlorotoluene. Typically, as chlorination proceeds beyond the stage of mono-chlorination, complex mixtures are produced in unequal proportions. Each catalyst reacts differently under the same or different reaction conditions so that catalytic results become impossible to predict. U.S. Pat. Nos. 3,226,447; 2,608,591 and 2,473,990 together with United Kingdom Pat. No. 778,642 point out these variations in results as to specific reactants and products utilizing varying catalysts and conditions. U.S. Pat. No. 3,366,698, provides disclosure of a specific prior art process wherein zirconium tetrachloride is the catalyst in a parachlorotoluene/$Cl_2$ reaction. The commercial scarcity of zirconium tetrachloride however, increases the cost of the process and accordingly dampens its commercial competiveness.

It is an object of this invention to provide an improved process for the production of dichlorotoluenes. It is also an object of this invention to provide an improved process for the production of dichlorotoluene containing a very high percentage of 2,4-dichlorotoluene. Another object of the present invention is to provide an improved process for the production of substantially pure 2,4-dichlorotoluene. An additional object of the instant invention is for the production of a dichlorotoluene product that contains a substantially high yield of 2,4-dichlorotoluene, of high purity, and with substantially less amounts of less desirable dichlorotoluene isomers, i.e. 3,4-dichlorotoluene and 2,5-dichlorotoluene, and of trichlorotoluene. A further object of this invention is to provide an improved process for the production of dichlorotoluene at a lower commercial cost.

The process of the present invention is carried out by contacting parachlorotoluene with chlorine in the presence of a catalytic amount of antimony trichloride catalyst. Since antimony pentachloride is generally present in some amount in a commercial antimony trichloride composition and further since antimony trichloride may react in the chlorination process to form the pentachloride, a distinction between the trichloride and pentachloride in this process would be inappropriate. Accordingly, it is understood, that use of the term antimony trichloride catalyst includes a composition which may comprise antimony pentachloride.

More particularly, the process of the present invention comprises contacting liquid parachlorotoluene with gaseous chlorine in a mole ratio of about 0.5 to about 1.5 in the presence of less than about 1.0 percent of a catalyst comprising antimony trichloride, antimony pentachloride and mixtures thereof, until completion of the reaction. The reaction product is thus treated with a base and the catalyst is removed by separation or filtration. The resulting product is then fractionally distilled to separate the dichlorotoluenes from unreacted parachlorotoluene and any trichlorotoluenes that may be present. The product recovered is substantially pure 2,4-dichlorotoluene, by substantially pure meaning a product containing in excess of 95% by weight of 2,4-dichlorotoluene.

Only a small amount of antimony trichloride catalyst need be present in a reaction mixture to increase the relevant amount of 2,4-dichlorotoluene that is formed. As little as 0.05% of the catalyst, based on the weight of parachlorotoluene, will bring about a substantial increase in the 2,4-dichlorotoluene content of the chlorination product. There appears to be no advantage in using more than about 3.0% by weight of the catalyst, the preferred range being from about 0.05 to 1.0% by weight catalyst.

While the antimony trichloride catalyst is ordinarily preferably used as the sole chlorination catalyst in the chlorination of parachlorotoluene, it may also be used in combination with catalysts such as iron, ferric chloride or zirconium tetrachloride. The chlorination may, for example, be carried out by adding a mixture of the antimony trichloride catalyst and iron or zirconium tetrachloride or other catalyst to the reaction mixture or by carrying out the chlorination of parachlorotoluene in the presence of the antimony trichloride catalyst in an iron vessel. The antimony trichloride catalyst has been found to be effective in promoting the formation of 2,4-dichlorotoluene in the presence of other catalysts.

The chlorination of parachlorotoluene may be carried out by procedures that are well known in the art. For example, chlorine may be added to a reaction mixture containing parachlorotoluene and the chlorination catalyst until the increase in the weight of the reaction mixture, or the specific gravity, indicates that the desired amount of chlorine has reacted with parachlorotoluene. In the practice of the present invention the chlorination is usually continued until reaction is complete. The reaction product generally contains in excess of 85% of dichlorotoluene and relatively small percentages of unreacted parachlorotoluene and trichlorotoluenes. The product of the chlorination is then treated with a base to remove the catalyst. Typical bases operable herewith include ammonia, organic amines, alkali and alkaline earth hydroxides, carbonates and bicarbonates. Preferred bases are anhydrous ammonia, sodium carbonate and organic amines. After treatment with a base the catalyst, or catalyst base complex, may be removed by separation or filtration. The dichlorotoluene fraction, which may be separated from the parachlorotoluene and trichlorotoluenes by fractional distillation or other known technique, contains a high percentage of 2,4-dichlorotoluene, in excess of 95%, the remainder being 3,4-dichlorotoluene.

The chlorination reaction may be carried out at temperatures in the range of from about 0° C to about 100° C, with about 20 to about 70° C the preferred temperature range. Below 0° C the reaction takes place too slowly to be of commercial interest. At temperatures above 100° C there is a tendency for side-chain chlorinated by-products and other by-products to be formed. Since chlorination is an exothermic reaction, external cooling may be required to maintain the reaction temperature in the desired range.

The rate at which chlorine is added to the reaction mixture does not have an appreciable effect on the yield of dichlorotoluene or the isomer distribution in the product.

The following examples are listed to illustrate this invention and to compare it with other standard chlorination catalysts under the same conditions. It should be understood however that these examples are given by way of illustration and not limitation. All temperatures are in degrees centigrade and all parts are by weight, unless otherwise indicated.

EXAMPLE 1

To a glass chlorination vessel containing 126.6 grams (1 mole) of parachlorotoluene, was added sufficient antimony trichloride catalyst to form a concentration of 1.0% by weight. Chlorine gas was then introduced to the chlorination vessel, from a weighed cylinder, and into the reaction mixture until said mixture had reacted with the $Cl_2$ in a mole ratio of 0.9 mole $Cl_2$/1 mole parachlorotoluene. The chlorination process was conducted at atmospheric pressure and the reaction mixture was mechanically stirred and externally cooled to maintain the reaction temperature at about 25° C. Upon completion of the reaction, the product was purged with nitrogen so as to remove residual HCl, anhydrous ammonia was bubbled into the reaction mixture to complex the catalyst and the insoluble catalyst complex was removed by filtration. Thereafter, the product was analyzed by gas chromatography to contain a dichlorotoluene fraction of 80.9% of theory, with the dichlorotoluene fraction containing 85.1% 2,4-dichlorotoluene. This represents a yield of 68.9% of theory.

EXAMPLES II – IV

The process of Example I was repeated using the delineated catalyst concentrations with the following tabulated results.

TABLE I

| Catalyst | | Conc. | Conversion Rate* of dichlorotoluene Fraction | % 2.4 in DOT Fraction | Yield 2.4 DOT |
|---|---|---|---|---|---|
| Ex. II | $SbCl_3$ | 1.0% | 80.2 | 84.5% | 67.7 |
| Ex. III | $SbCl_3$ | 0.5% | 79.0 | 63.3% | 65.7 |
| Ex. IV | $SbCl_3$ | 0.25% | 79.4 | 53.7% | 66.4 |

*Calculated as percent of theory

EXAMPLES V – XI

The process of Example I was repeated using several prior art chlorination catalysts with results as tabulated below.

TABLE II

| Catalyst | | Conc. | Conversion Rate* of Theory dichlorotoluene Fraction | % 2,4 in DOT Fraction | Yield 2.4 DOT |
|---|---|---|---|---|---|
| Ex. V | $SbCl_3$ | 1.0% | 80.9 | 85.1 | 66.9 |
| Ex. VI | $ZrCl_4$ | 1.0% | 79.4 | 83.6 | 66.4 |
| Ex. VII | $MoCl_5$ | 1.0% | 77.1 | 51.5 | 62.7 |
| Ex. VIII | $FeCl_3$ | 1.0% | 72.9 | 80.2 | 55.4 |
| Ex. IX | $I_2$ | 1.0% | 71.1 | 75.7 | 53.9 |
| Ex. X | $TiCl_3$ | 1.0% | 69.7 | 70.5 | 49.2 |
| Ex. XI | $Fe_2S_3$ | 1.0% | 66.8 | 59.1 | 39.5 |

*Calculated as percent of theory

EXAMPLE XII

The process of Example I was repeated, operating the chlorination process at 55° C. The product analyzed as containing a dichlorotoluene fraction of 81.7% of theory with a content of 83.7% 2,4-dichlorotoluene. This represents a yield of 68.4% of theory.

I claim:
1. An improved process for the production of 2,4-dichlorotoluene comprising the steps of
   1. reacting para-chlorotoluene, in the liquid phase, with gaseous chlorine in a mole ratio of about 0.5:1 to about 1.5:1 at a temperature from about 0° to about 100° C in the presence of from about 0.05% to about 3.0% by weight of a catalyst consisting of antimony trichloride to yield a product containing 2,4-dichlorotoluene;
   2. treating the product of step (1) with anhydrous ammonia and removing the catalyst by filtration; and
   3. distilling the product of Step (2) to yield substantially pure 2,4-dichlorotoluene.

2. The process of claim 1 wherein the product of step (2) is distilled to contain in excess of 95% by weight 2,4-dichlorotoluene.

3. The process of claim 1 wherein said catalyst is present in an amount from about 0.05% to about 1.0% by weight.

4. The process of claim 1 wherein Step 1 is conducted at a temperature from about 20° to about 70° C.

* * * * *

UNITED STATES PATENT AND TRADEMARK OFFICE
CERTIFICATE OF CORRECTION

PATENT NO. : 4,006,195

DATED : February 1, 1977

INVENTOR(S) : Samuel Gelfand

It is certified that error appears in the above—identified patent and that said Letters Patent are hereby corrected as shown below:

Column 4, Table I, lines 10 and 11, and Table II, lines 26 and 27, "DOT" should read ---DCT---; Table I, Ex. III, "63.3%" should read --83.3%--; Ex. IV, "53.7%" should read --83.7%--; Table II, Ex. X, "TiCl$_3$" should read --TiCl$_4$--; Table II, Ex. VII, "51.5" should read --81.5--; Table II, Ex. V, "Yield 66.9" should read --Yield 68.9--; Ex. VIII, "Yield 55.4" should read --Yield 58.4--.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*